(12) United States Patent
Koschmieder

(10) Patent No.: US 7,938,016 B2
(45) Date of Patent: May 10, 2011

(54) MULTIPLE LAYER STRAIN GAUGE

(75) Inventor: Thomas H. Koschmieder, Austin, TX (US)

(73) Assignee: Freescale Semiconductor, Inc., Austin, TX (US)

( * ) Notice: Subject to any disclaimer, the term of this patent is extended or adjusted under 35 U.S.C. 154(b) by 193 days.

(21) Appl. No.: 12/408,442

(22) Filed: Mar. 20, 2009

(65) Prior Publication Data

US 2010/0236334 A1    Sep. 23, 2010

(51) Int. Cl.
*G01N 19/08* (2006.01)
*G01B 7/16* (2006.01)

(52) U.S. Cl. ............... 73/799; 73/777; 257/619

(58) Field of Classification Search ............ 73/760–799; 257/619
See application file for complete search history.

(56) References Cited

U.S. PATENT DOCUMENTS

| | | | |
|---|---|---|---|
| 4,658,233 A | 4/1987 | Uchida et al. | |
| 5,417,115 A | 5/1995 | Burns | |
| 5,608,172 A | 3/1997 | De Magalhaes Machado et al. | |
| 5,804,771 A * | 9/1998 | McMahon et al. | 174/255 |
| 5,946,549 A | 8/1999 | Itoigawa et al. | |
| 6,314,815 B1 * | 11/2001 | Avisse | 73/708 |
| 6,332,359 B1 * | 12/2001 | Ueyanagi et al. | 73/514.33 |
| 6,667,127 B2 * | 12/2003 | Beattie et al. | 429/535 |
| 6,739,199 B1 | 5/2004 | Nikkel | |
| 6,770,164 B1 * | 8/2004 | Schrock et al. | 156/306.9 |
| 6,928,879 B2 | 8/2005 | Partridge et al. | |
| 7,129,566 B2 * | 10/2006 | Uehling et al. | 257/620 |
| 7,208,841 B2 | 4/2007 | Wang et al. | |
| 7,432,221 B2 * | 10/2008 | Kim et al. | 502/185 |
| 7,687,915 B2 * | 3/2010 | Lee et al. | 257/758 |
| 7,744,740 B2 * | 6/2010 | Diehl | 205/784.5 |
| 2003/0146502 A1 * | 8/2003 | Parsons | 257/703 |
| 2006/0024558 A1 * | 2/2006 | Friedman et al. | 429/38 |

* cited by examiner

*Primary Examiner* — Max Noori
(74) *Attorney, Agent, or Firm* — Charles Bergere; Kim Marie Vo

(57) ABSTRACT

An apparatus and method uses a die having at least one perimeter side with multiple pads. A structure is positioned between the at least one perimeter side and the multiple pads having multiple layers within the die. The structure functions as both a strain gauge and a crack stop. The structure arrests cracks from propagating from the at least one perimeter side to an interior of the die and provides an electrical resistance value as a function of an amount of strain existing where the structure is positioned. In another form the structure is implemented on a substrate such as a printed circuit board rather than in a semiconductor die.

17 Claims, 4 Drawing Sheets

MULTIPLE LAYER STRAIN GAUGE

BACKGROUND

1. Field

This disclosure relates generally to forming a strain gauge, and more specifically, to forming a multiple layer strain gauge.

2. Related Art

Integrated circuits may be exposed to strain when the package is introduced into an environment with temperature changes, such as an integrated circuit used in a car or a computer. Extreme temperature changes may create enough strain to cause the integrated circuits to fail. Thus, manufacturers of integrated circuits want to understand how their packaged integrated circuits withstand strain in certain temperature ranges so that they can build reliable products. Hence, manufacturers often run tests to try to determine the strain the package experiences under predetermined conditions. However, measuring strain of a packaged integrated circuit is difficult. External strain gauges are used but they are large compared to the packaged integrated circuits. At best overall strain can be measured and strain at localized areas cannot be determined. Also, due to their large size, the strain gauges often do not fit into the electrical test systems used to determine product functionality. Hence, there is a need for a way to measure strain of integrated circuit packages.

BRIEF DESCRIPTION OF THE DRAWINGS

The present invention is illustrated by way of example and is not limited by the accompanying figures, in which like references indicate similar elements. Elements in the figures are illustrated for simplicity and clarity and have not necessarily been drawn to scale.

DETAILED DESCRIPTION

A multiple layer strain gauge can be formed as a part of an integrated circuit die or as a discrete device on a printed circuit board (PCB). The multiple layer strain gauge allows for in-situ monitoring of strain in the integrated circuit or the PCB during testing or other processes. Strain is a ratio of the change in dimension (e.g., length) relative to the original dimension. In contrast, stress is a measure of the force over a given area.

If the multiple layer strain gauges are formed as part of an integrated circuit die it may also serve as a crack arrest feature. The output of the strain may be monitored and used to determine when to set off an alarm, if a heat sink is improperly aligned, or when to terminate a process (e.g., testing), etc. In addition, the strain may be used to determine a strain threshold for when a package is likely to fail during thermal testing. In one embodiment, the multiple layer strain gauge allows for a corner of a die to be monitored for delamination during qualification. Thus, an early warning may be provided for integrated circuit die including final electronic packages that will fail due to excessive strain levels in corners. In addition, a reliability test for customer returned parts may be created. Also, a way to sort products during electric test to weed out weak products may be created.

Figure 1:
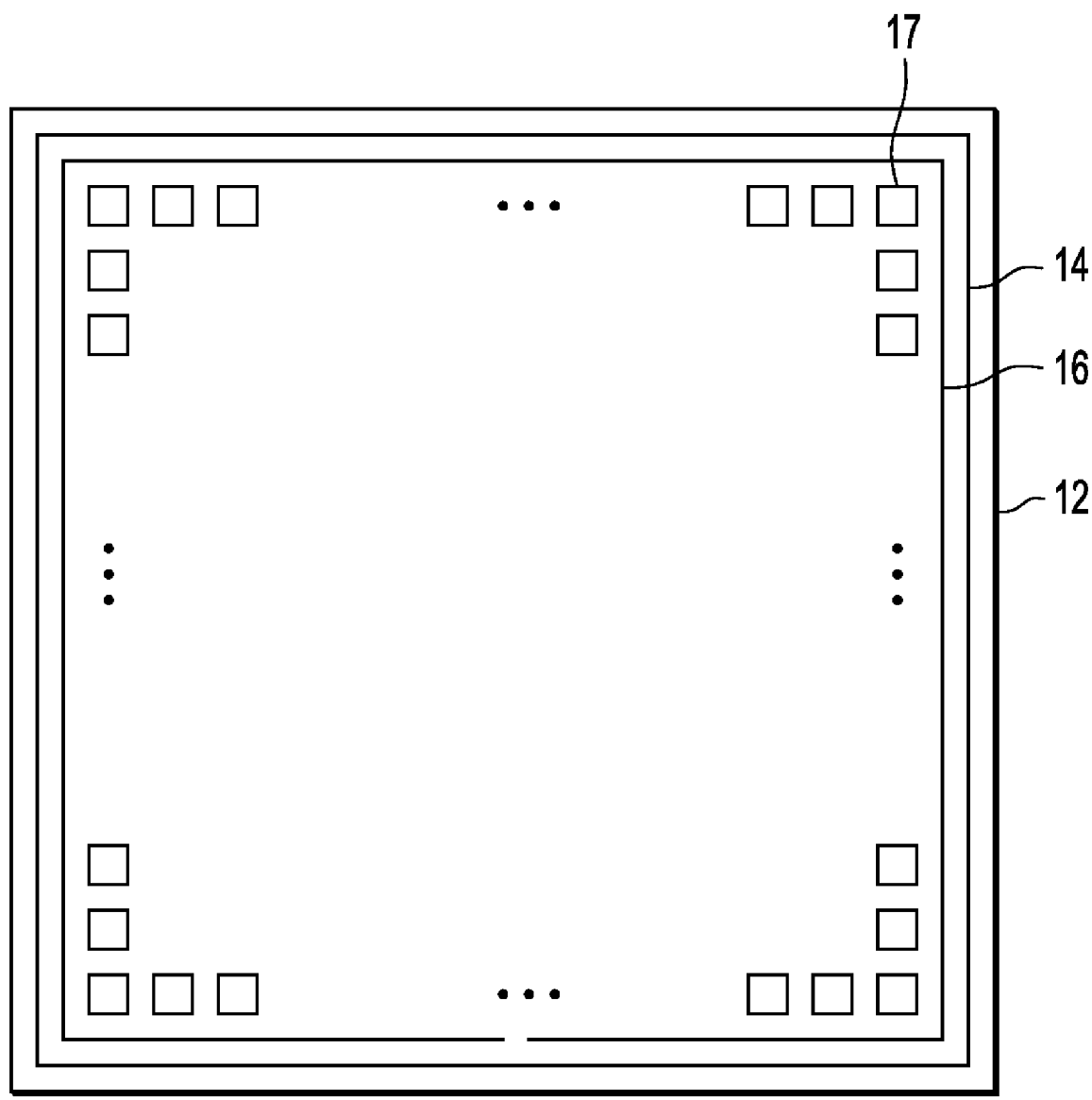
FIG. 1 illustrates a top-down view of an integrated circuit die in accordance with embodiments of the present invention.

FIG. 1 illustrates a top-down view of an integrated circuit die 10 in accordance with embodiments of the present invention. The integrated circuit die 10 can be any type of integrated circuit, such as a microcontroller, a microprocessor, a digital signal processor, a sensor, the like, or combinations of the above. In one embodiment, the integrated circuit die 10 includes, a perimeter or periphery 12, a crack arrest feature 14, a strain gauge 16, and pads 17. The integrated circuit die 10 has perimeter sides. In the embodiment illustrated, the integrated circuit die 10 has four perimeter sides that make up the perimeter. The pads 17 are farther from the perimeter 12 than the crack arrest feature 14 and the strain gauge 16. The crack arrest arrests cracks from propagating from at least one perimeter side of a die to an interior of the die. The strain gauge 16 provides an electrical resistance value as a function of an amount of strain existing where the strain gauge 16 is positioned. In one embodiment, the pads 17 are wirebond pads and in another embodiment, the pads 17 are pads in a flip chip device. In both embodiments, additional pads than those illustrated in FIG. 1 may be formed between the illustrated pads 17. In one embodiment, the strain gauge 16 is parallel to the perimeter 12. The strain gauge 16 is not continuous. A break as illustrated in FIG. 1 is present so that the strain gauge does not short itself. In another embodiment, the strain gauge 16 is not present and the crack arrest 14 is both a crack arrest and a strain gauge (i.e., a composite crack arrest and strain gauge). In this embodiment, the crack arrest and strain gauge 14 would not be continuous; a break similar to the break illustrated in element 16 of FIG. 1 would be present. In yet another embodiment, the crack arrest 14 is both a crack arrest and a strain gauge and an additional crack arrest structure is present. In this embodiment, the crack arrest structure may be between the composite crack arrest and strain gauge 14 and at least a side of the die.

Figure 2:
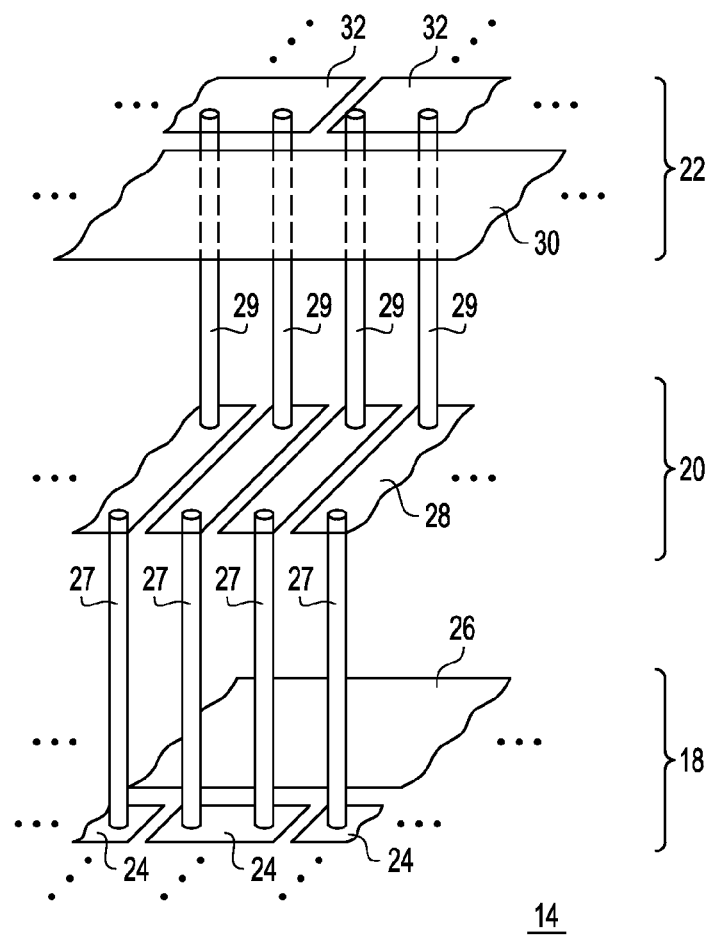
FIG. 2 illustrates a cross-section of a portion of a crack arrest and strain gauge in accordance with an embodiment.

FIG. 2 illustrates a cross-section of a portion of a crack arrest and strain gauge 14 in accordance with an embodiment. FIG. 2 illustrates three layers of the crack arrest and strain gauge 14: a first layer 18, a second layer 20, and a third layer 22. However, any number of layers greater than one may be present (e.g., 3, 5, 8, 9, etc. layers.) The layers 18, 20 and 22 may be any conductive material that changes an electrical resistance value when the length of the material changes (e.g., copper). The first layer 18 includes a strain gauge and crack arrest portion 24 and a crack arrest portion 26. The strain gauge and crack arrest portion 24 includes several portions separated by dielectric because without such separation the current, which will choose the shortest path, would travel along the horizontal direction in each layer as opposed to traveling in the vertical direction as desired. Hence, the strain gauge and crack arrest portions 24 have physically separated sections, where all sections are electrically coupled but physically adjacent sections in the same layer are not directly connected to each other. For the same reason that the strain gauge and crack arrest portions 24 have physically separate sections, a dielectric separates the strain gauge and crack arrest portion 24 from the crack arrest portion 26. The strain gauge and crack arrest portion 24 act as both i) a strain gauge by measuring strain of the die or portions of the die and ii) a crack arrest portion 24 by stopping or minimizing the propagation of cracks from traveling from the perimeter of the die towards the center of the die. In contrast, the crack arrest portion 26 acts only as a crack arrest portion. In the embodiment illustrated, the crack arrest portion 26 is not coupled to vias or other strain gauge and crack arrest portions, but they can be. The crack arrest portions can be continuous layers that cover all areas of the die except for the portion covered by the crack arrest and strain gauge portions and the dielectric between the crack arrest and strain gauge and itself. In another embodiment, the crack arrest portions are only formed in a portion of the die. Also, because electrical performance is not a concern for the crack arrest portion 26, it can be a larger continuous piece of, e.g. conductive, material than the strain gauge and crack arrest portion 24. This helps to better minimize crack propagation than the smaller strain gauge and crack arrest portions 24. Vias 27 couple the strain gauge and crack arrest portions 24 to strain gauge and crack arrest portions 28 in the second layer 20. The strain gauge and crack arrest portions 24 are perpendicular to the strain gauge and crack arrest portions 28. Furthermore, although not illustrated, the second layer 20 may include a crack arrest portion. The strain gauge and crack arrest portions 28 of the second layer 20 are coupled to the strain gauge and crack arrest portions 32 of the third layer 22, which also includes the crack arrest feature 30. The strain gauge and crack arrest portions 32 are perpendicular to the strain gauge and crack arrest portions 28.

It is not necessary that the strain gauge and crack arrest portions within each layer are perpendicular to the strain gauge and crack arrest portions in adjacent layers. However, if at least each layer has two or more vias, then at least two layers have parts of the strain gauge and crack arrest portions that are perpendicular to parts of strain gauge and crack arrest portions in other layers so that the strain gauge can be connected throughout all the layers. Other parts of the strain gauge and crack arrest can be parallel to parts of the strain gauge and crack arrest portions in the other layer. In other words, a strain gauge and crack arrest portion may have at least one part that are perpendicular to and at least another part that is parallel to a strain gauge and crack arrest portion in another layer. Either the strain gauge and crack arrest portions or the vias may function as the strain gauge. Which one is the strain gauge will be determined by making it the longest path because the longest length is parallel to the direction that one wants to measure strain. (Hence, the via lengths or the lengths of the strain gauge and crack arrest portions will be longest in the direction in which one wants to measure strain.) In one embodiment, the plurality of vias 27, 29 have a direction in which strain is measured that is perpendicular to at least two adjoining layers 24, 28 or 28, 32.

Any number of vias 27 or 29 can be formed to coupled strain gauge and crack arrest portions of the different layers. Furthermore, although the vias 27 and 29 are not located over each other, the vias can be located over each other and hence appear as one continuous via. In the embodiment where the strain gauge does not also serve as a crack arrest, the crack arrest portions 26 and 30 may not be present and the crack arrest and strain gauge portions 24, 28, and 32 are strain gauge portions.

Figure 3:
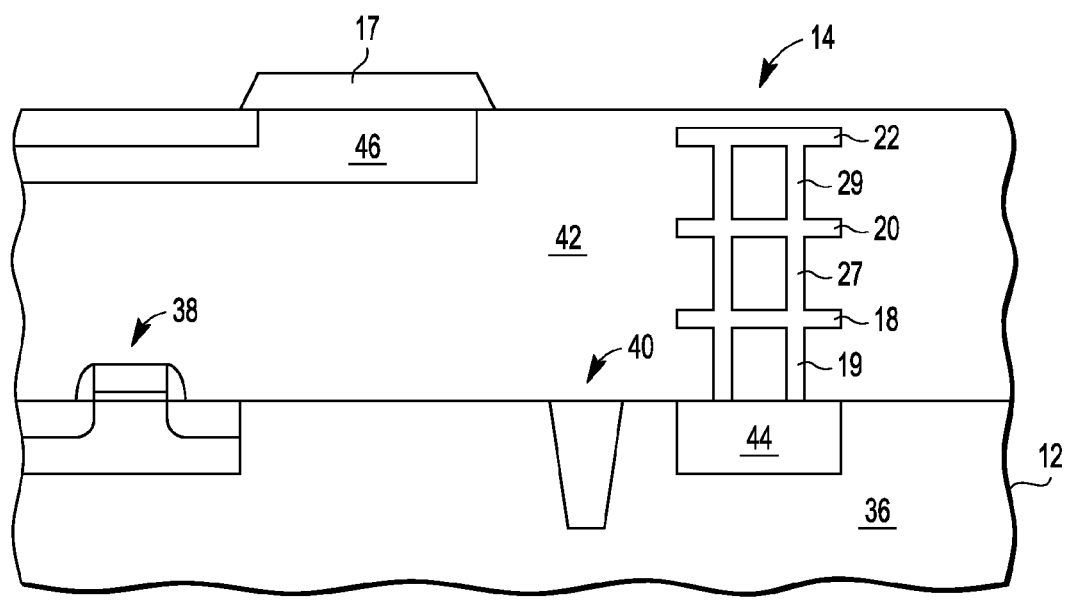
FIG. 3 illustrates a cross-section of a portion of an integrated circuit die having a crack arrest and strain gauge in accordance with an embodiment.

FIG. 3 illustrates a cross-section of a portion of die having a crack arrest and strain gauge 14 in accordance with an embodiment. In the embodiment illustrated, vias 19 are part of the strain gauge 14 of FIG. 3 although they are not illustrated in FIG. 2. Vias 19 are similar to vias 27 and 29. In one embodiment, the crack arrest and strain gauge 14 is a strain gauge 14 and does not also serve as a crack arrest. The crack arrest and strain gauge 14 is adjacent to the perimeter or edge 12 of the integrated circuit die 34 and is closer to the edge 12 than isolation region 40, pad 17, or transistor 38. The crack arrest and strain gauge 14 may be electrically coupled to a substrate 36, which may be a semiconductor substrate. In one embodiment, the crack arrest and strain gauge 14 is coupled to the substrate 36 through a high conductivity region 44. The high conductivity region 44 has a conductivity that is greater than the substrate 36, which may be silicon. In the embodiment illustrated, the high conductivity region 44 may be a region doped n or p-type. The high conductivity region 44 is in direct contact with the crack arrest and strain gauge 14. The pad 17 is coupled to a conductive path 46 that electrically couples the pad 17 to circuitry (not illustrated.) The transistor 38 may be any type of transistor. The trench isolation 40 may be any suitable isolation, such as a shallow trench isolation region. The trench isolation 40 electrically separates the transistor 38 from the strain gauge 14. The trench isolation 40 may not be present. A dielectric 42, which includes many different dielectric layers, electrically isolates portions of the crack arrest and strain gauge 14 from each other. The integrated circuit die 34 of FIG. 3 may be packaged using any suitable process. For example, the die 34 may be coupled to a packaging substrate, a wirebond may be attached to the pad 17 and a pad on the packaging substrate, and a mold encapsulant may be formed over the integrated circuit die 34 and the packaging substrate and along the edge 12 to form a wirebond package. Alternatively, other packages, such as flip-chip packages may be formed.

Figure 4:
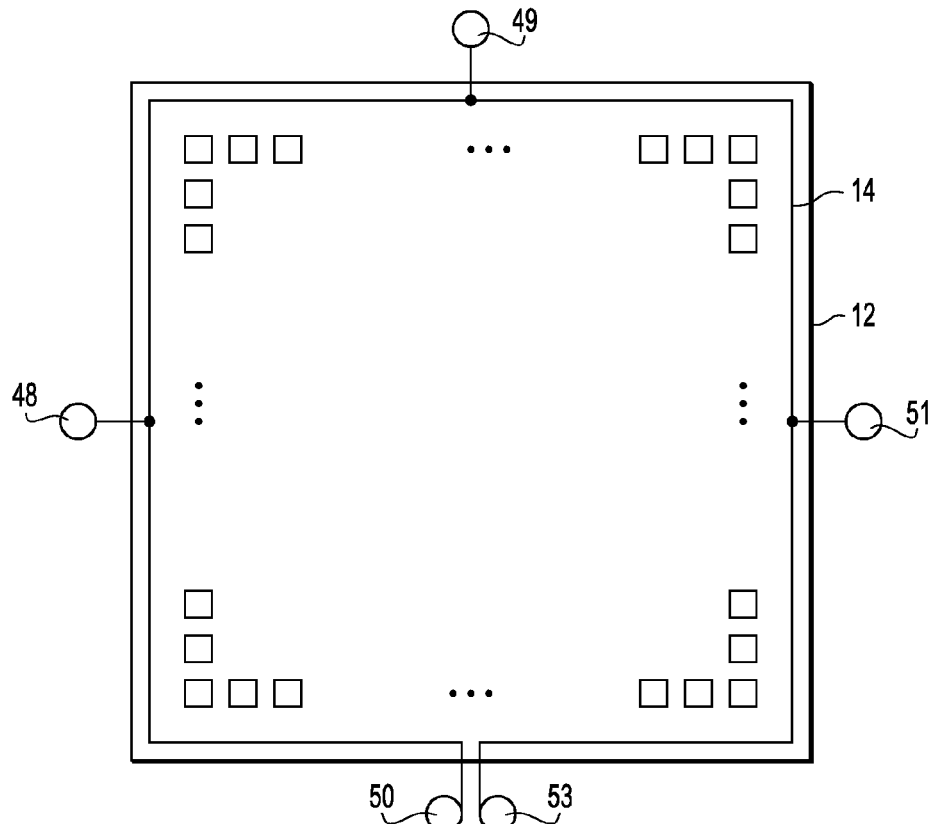
FIG. 4 illustrates a top-down view of an integrated circuit die having strain gauge terminals in accordance with an embodiment.

FIG. 4 illustrates a top-down view of an integrated circuit die 11 having strain gauge terminals 48, 50 in accordance with an embodiment. Each strain gauge terminal 48, 50 is electrically coupled to the crack arrest and strain gauge 14. Although five terminals are illustrated in FIG. 4 any number of terminals greater than or equal to 2 may be used to determine the strain of the die or portions of the die 11. The strain of the regions between the two terminals that are contacted is measured. For example, if the both terminals 50 and 53 are contacted, then strain over the entire die 11 is measured. Instead, if terminal 48 and terminal 49 are contacted then the stain in the upper left quadrant of the die 11 is measured. If terminals 49 and 51 are contacted, then the strain of the upper right quadrant of the die 11 is measured. If the terminals 51 and 53 are contacted, then the strain of the lower right quadrant of the die is measured. If the terminals 50 and 48 are contacted, then the lower left quadrant of the die is measured. If the terminals 48 and 51 are contacted then the strain of the top half of the die 11 is measured. If the terminals 49 and 50 are contacted then the strain of the left half of the die 11 is measured. If the terminals 49 and 53 are contacted then the strain of the right half of the die 11 is measured. Other portions of the die can be measured by contacting other combinations of the terminals.

Figure 5:
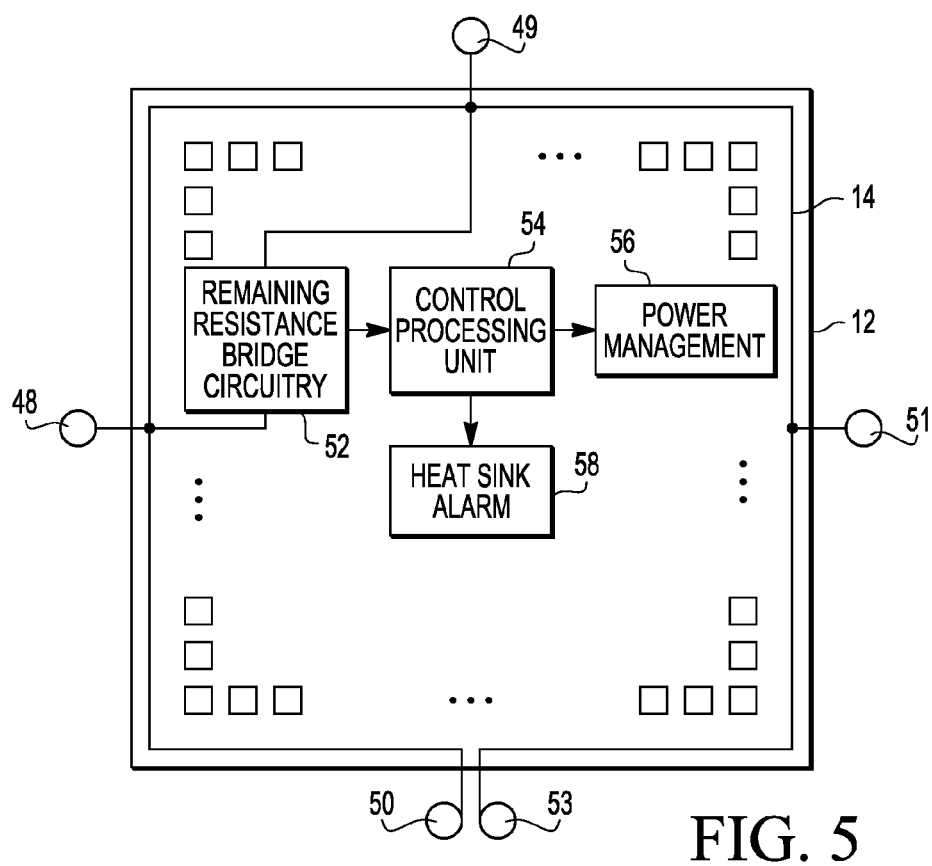
FIG. 5 illustrates a top-down view of an integrated circuit die with exemplary circuitry in accordance with an embodiment.

FIG. 5 illustrates a top-down view of an integrated circuit die 13 with exemplary circuitry in accordance with an embodiment. The exemplary circuitry is a plurality of integrated circuits formed on the integrated circuit die 13 for implementing a predetermined function. In the embodiment illustrated, terminals 48 and 49 are coupled to a remaining resistance bridge circuitry 52. (However, other terminals may be coupled to the remaining resistance bridge circuitry 52.) The resistance bridge circuitry 52 may include resistors and a voltage source, as will be explained further in regards to FIG. 7. The remaining resistance bridge circuitry 52 sends the strain gauge information, which in this embodiment is the strain of the top left corner of the die 13, to control processing unit 54. The control processing unit 54 may determine whether a measured strain value is within a predetermined range of values. The control processing unit 54 may compare the strain gauge information to a predetermined strain gauge threshold. If the strain gauge information is greater than the strain gauge threshold, the control processing unit 54 may send a signal to a power management unit 56, which then may stop the process (e.g., a test) that is causing the strain. In one embodiment, the power management unit controls either a power supply voltage value for operating the die or an operating frequency of a structure formed within the semiconductor substrate of the die. In one embodiment, the control processing until 54 determines if all the terminals are in equilibrium and if not, it sends a message to the heat sink alarm 58. The heat sink alarm 58 may provide an alarm related to dissipation of heat generate by the semiconductor substrate. For example, the heat sink alarm may provide a notification that the heat sink is not properly attached. This alarm may be a sound, a visual alarm, a text message, the like, or combinations of the above.

Figure 6:
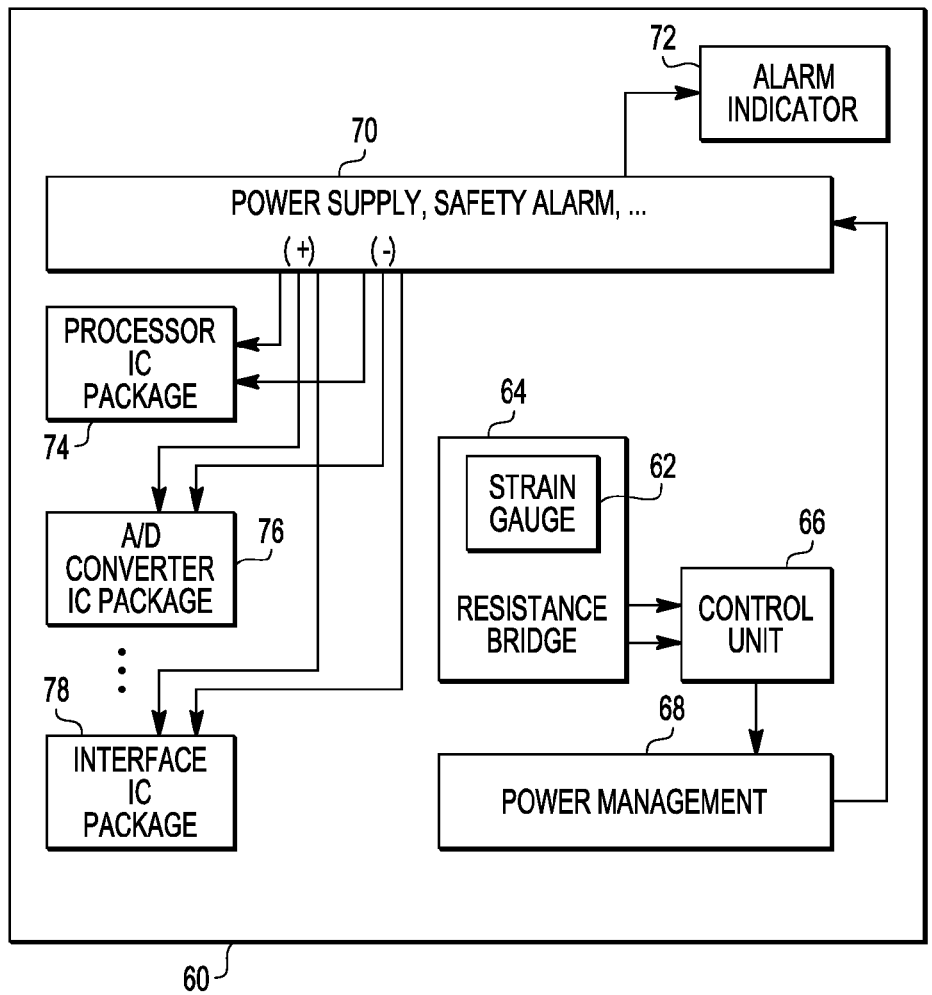
FIG. 6 illustrates a printed circuit board with exemplary circuitry in accordance with an embodiment.

FIG. 6 illustrates a printed circuit board (PCB) 60 having exemplary circuitry in accordance with an embodiment. The exemplary circuitry is a plurality of integrated circuits formed on the PCB 60 for implementing a predetermined function. In one embodiment, the PCB 60 may be subject to a bending motion, for example. The PCB 60 includes a resistance bridge 64 that includes a strain gauge 62. If the PCB 60 is bending, the resistance bridge 64 will measure the strain of the PCB 60 and send the measurement to the control unit 66. The control unit 66, like the control processing unit 54 of FIG. 5, may compare the measured strain to a predetermined threshold. For example, if the strain is over a predetermined threshold, the control unit 66 may send a signal to the power management 68 which may do among other things, send a signal to shut off or change the power supply 70 to stop the bending process or to send a signal the safety alarm 70 that an alarm should be triggered. If the safety alarm receives a signal to trigger the alarm, it will send a signal to the alarm indicator 72, which can be an audio alarm, a visual alarm, a text message, the like, or combinations of the above. The power supply/safety alarm 70 may be electrically coupled to a processor IC package 74, an A/D converter IC package 76, an interface IC package 78, the like, or combinations of the above. If the power supply 70 receives signal to stop the processing, it may send a signal to one of the IC packages 74, 76, or 78 to shut down. A skilled artisan appreciates that for simplicity all of the routing and connections, such as the PCB's 60 connections and ports are not illustrated.

Figure 7:
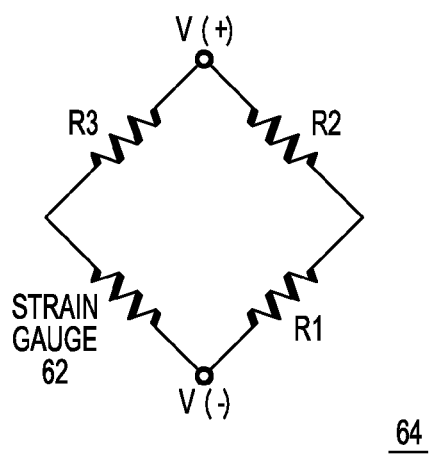
FIG. 7 illustrates a resistance bridge in accordance with an embodiment.

FIG. 7 illustrates a resistance bridge 64 in accordance with an embodiment. The resistance bridge illustrated is a Wheatstone bridge where one resistor is replaced with the strain gauge 62. A Wheatstone bridge is a measuring apparatus that measures an unknown electrical resistance through balancing two legs of a bridge circuit, where one leg includes the unknown electrical resistance by using ratios of the resistances. The resistance bridge 64 includes three resistors and the strain gauge 62. For example, the resistance bridge 64 can be balanced by balancing one leg that includes the R1 and R2 and the other leg includes R3 and the strain gauge 62. The voltage difference between the terminals marked (+) and (−) will be zero if the two legs of the bridge circuit are balanced and hence no current will flow. A measuring instrument (not illustrated), such as a galvanometer or the like, may be used to measure the voltage difference across the terminals. For illustrative purposes the figures have shown the strain gage to be in the die or PCB while the rest of the Wheatstone bridge resistors are located separately. However, one or more of the resistors of the resistance Wheatstone bridge may be located on the die itself. These resistors may also be strain gauge and crack arrest portions.

Unless stated otherwise, terms such as "first" and "second" are used to arbitrarily distinguish between the elements such terms describe. Thus, these terms are not necessarily intended to indicate temporal or other prioritization of such elements. The term "coupled," as used herein, is not intended to be limited to a direct coupling or a mechanical coupling. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

What is claimed is:

1. A semiconductor comprising:
    a die having at least one perimeter side with multiple pads; and
    a structure positioned between the at least one perimeter side and the multiple pads, wherein the structure has multiple layers within the die and the structure functions as both a strain gauge and a crack stop, the structure arresting cracks from propagating from the at least one perimeter side to an interior of the die and providing an electrical resistance value as a function of an amount of strain existing where the structure is positioned,
    wherein the strain gauge comprises a plurality of vias, each of the plurality of vias connecting at least two adjoining layers of the multiple layers of the structure, wherein the plurality of vias extend in a direction in which strain is measured that is perpendicular to the at least two adjoining layers.

2. The semiconductor of claim 1, wherein each of the multiple layers of the structure further comprises an electrically conductive strain gauge portion, one or more predetermined electrically conductive strain gauge portions having multiple physically separated sections, wherein all sections are electrically coupled but physically adjacent sections in a same layer are not directly connected to each other.

3. The semiconductor of claim 2 further comprising:
    an additional crack arrest structure that is positioned between the structure and the at least one perimeter side, the additional crack arrest structure providing additional crack arrest protection for the die.

4. The semiconductor of claim 1, further comprising:
an additional crack arrest structure that is positioned between the structure and the at least one perimeter side, the additional crack arrest structure providing additional crack arrest protection for the die.

5. The semiconductor of claim 1 wherein the structure is used as a portion of a resistance bridge for providing an output that is proportional to strain within the semiconductor at the structure, the semiconductor further comprising:
a control processing unit coupled to the resistance bridge, the control processing unit determining whether a measured strain value is within a predetermined range of values; and
a power management unit coupled to the control processing unit, the power management unit controlling either a power supply voltage value for operating the semiconductor or an operating frequency of the semiconductor.

6. The semiconductor of claim 1 wherein the structure is used as a portion of a resistance bridge for providing an output that is proportional to strain within the semiconductor at the structure, the semiconductor further comprising:
a control processing unit coupled to the resistance bridge, the control processing unit determining whether a measured strain value is within a predetermined range of values; and
a heat sink alarm coupled to the control processing unit, the heat sink alarm providing an alarm related to dissipation of heat generated by the semiconductor.

7. The semiconductor of claim 1 further comprising:
a substrate underlying the structure; and
a high conductivity region within the substrate, the high conductivity region being in direct contact with the structure.

8. The semiconductor of claim 7, further comprising:
a transistor, a portion of which is formed in the substrate; and
an isolation region within the substrate, the isolation region electrically separating the transistor from the structure.

9. An apparatus, comprising:
a substrate having a plurality of integrated circuits formed thereon for implementing a predetermined function;
a strain gauge structure positioned on the substrate, the strain gauge structure providing a resistance value as a function of an amount of strain existing where the strain gauge structure is positioned;
a resistance bridge positioned on the substrate and using the resistance value of the strain gauge structure to provide a voltage that is proportional to strain existing within the substrate in a direction that is either perpendicular to or parallel to a top surface of the substrate;
a control unit coupled to the resistance bridge, the control unit providing a control signal related to operation of the apparatus; and
a power management unit coupled to the control unit, the power management unit adjusting an operating voltage or an operating frequency of at least one of the plurality of integrated circuits in response to the control signal indicating that the strain existing within the substrate has exceeded a predetermined threshold.

10. The apparatus of claim 9 further comprising:
a heat sink alarm coupled to the control unit, the heat sink alarm providing an alarm related to dissipation of heat generated by the plurality of integrated circuits.

11. The apparatus of claim 9 wherein the strain gauge structure further comprises:
multiple layers, each of the multiple layers of the strain gauge structure further comprising an electrically conductive strain gauge portion, one or more predetermined electrically conductive strain gauge portions having multiple physically separated sections wherein one or more conductive vias electrically connect two sections from different layers, wherein all sections are electrically coupled but physically adjacent sections in a same layer are not directly connected to each other.

12. A method, comprising:
providing a semiconductor substrate having a perimeter side;
providing a composite crack stop and strain structure adjacent the perimeter side and between a pad and the perimeter side; and
providing a high conductivity region within the semiconductor substrate, the high conductivity region being in direct contact with the composite crack stop and strain structure.

13. The method of claim 12 further comprising:
providing multiple layers within the composite crack stop and strain structure, each of the multiple layers of the composite crack stop and strain structure further comprising an electrically conductive strain gauge portion, one or more predetermined electrically conductive strain gauge portions having multiple physically separated sections wherein one or more conductive vias electrically connect two sections from different layers, wherein all sections are electrically coupled but physically adjacent sections in a same layer are not directly connected to each other.

14. The method of claim 12 further comprising:
providing multiple layers within the composite crack stop and strain structure; and
electrically coupling a plurality of conductive vias, each of the plurality of conductive vias connecting at least two adjoining layers of the multiple layers of the composite crack stop and strain structure, the plurality of conductive vias having a direction in which strain is measured that is perpendicular to the at least two adjoining layers.

15. The method of claim 12 further comprising:
providing an additional crack arrest structure that is positioned between the composite crack stop and strain structure and the at least one perimeter side, the additional crack arrest structure providing additional crack arrest protection.

16. The method of claim 12 further comprising:
coupling the composite crack stop and strain structure as a portion of a resistance bridge for providing an output that is proportional to strain of the semiconductor substrate at the composite crack stop and strain structure;
coupling a control processing unit to the resistance bridge, the control processing unit determining whether a measured strain value is within a predetermined range of values; and
coupling a power management unit to the control processing unit, the power management unit controlling either a power supply voltage value for operating the apparatus or an operating frequency of a structure formed within the semiconductor substrate.

17. The method of claim 12 further comprising:
coupling the composite crack stop and strain structure as a portion of a resistance bridge for providing an output that is proportional to strain within the semiconductor substrate at the composite crack stop and strain structure;
coupling a control processing unit to the resistance bridge, the control processing unit determining whether a measured strain value is within a predetermined range of values; and
coupling a heat sink alarm to the control processing unit, the heat sink alarm providing an alarm related to dissipation of heat generated by the apparatus.

* * * * *